(12) United States Patent
Herrmann

(10) Patent No.: US 7,638,779 B2
(45) Date of Patent: Dec. 29, 2009

(54) MEDICAL RADIOTHERAPY ASSEMBLY

(75) Inventor: Klaus Herrmann, Nuremberg (DE)

(73) Assignee: Siemens Aktiengesellschaft (DE)

( * ) Notice: Subject to any disclaimer, the term of this patent is extended or adjusted under 35 U.S.C. 154(b) by 228 days.

(21) Appl. No.: 11/632,676

(22) PCT Filed: Sep. 19, 2005

(86) PCT No.: PCT/EP2005/054665

§ 371 (c)(1),
(2), (4) Date: Jan. 17, 2007

(87) PCT Pub. No.: WO2006/034973

PCT Pub. Date: Apr. 6, 2006

(65) Prior Publication Data

US 2007/0230660 A1    Oct. 4, 2007

(30) Foreign Application Priority Data

Sep. 30, 2004   (DE) ................. 10 2004 048 216
Dec. 23, 2004   (DE) ................. 10 2004 062 473

(51) Int. Cl.
*A61N 5/10*         (2006.01)
(52) U.S. Cl. .............. 250/491.1; 250/492.1; 250/492.3; 600/1; 600/2
(58) Field of Classification Search ............ 250/492.3, 250/492.1, 491.1; 600/413, 411, 407, 1, 600/2, 3, 4, 8, 310, 312, 427, 436, 440; 378/15, 378/20, 62, 63, 64, 65, 94, 95, 98, 152, 153, 378/176, 178, 179, 195, 196, 197, 198
See application file for complete search history.

(56) References Cited

U.S. PATENT DOCUMENTS 4,894,855 A    1/1990   Kresse (Continued)

FOREIGN PATENT DOCUMENTS

DE        196 25 407 A1    1/1998

(Continued)

OTHER PUBLICATIONS

Kamada T. Et al: "A horizontal CT system dedicated to heavy-ion beam treatment" Radiotherapy and Oncology Elsevier Ireland, vol. 50, No. 2, Feb. 1999, pp. 235-237, XP002359765.

(Continued)

*Primary Examiner*—Nikita Wells
*Assistant Examiner*—Nicole Ippolito Rausch
(74) *Attorney, Agent, or Firm*—Brinks Hofer Gilson & Lione

(57) ABSTRACT

The invention relates to a radiotherapy assembly comprising a particle emitter (2) with an exit window (4) for a fixed particle stream (6) and a patient support device (16) comprising a patient couch (18A, 18B), which can be brought into an irradiation position that is suitable for irradiating a patient (22) in front of the exit window (4). An X-ray diagnostic device (8) determines or verifies the position of a tumour that is to be irradiated, said device (8) comprising an X-ray source (12) and a detector (14), which can be displaced in the area around the patient couch (18A, 18B) that has been placed in the irradiation position. The assembly permits the location of a tumour to be verified in the irradiation position, thus rendering a relocation of the patient unnecessary.

17 Claims, 5 Drawing Sheets

U.S. PATENT DOCUMENTS

| | | | |
|---|---|---|---|
| 5,050,204 A | | 9/1991 | Siczek et al. |
| 5,321,271 A | * | 6/1994 | Schonberg et al. ........ 250/492.3 |
| 5,548,625 A | * | 8/1996 | Waldo, III .................... 378/34 |
| 5,901,200 A | | 5/1999 | Krause |
| 6,119,034 A | | 9/2000 | Herrmann et al. |
| 6,213,638 B1 | | 4/2001 | Rattner |
| 6,435,715 B1 | | 8/2002 | Betz et al. |
| 6,628,977 B2 | | 9/2003 | Graumann et al. |
| 6,811,313 B2 | * | 11/2004 | Graumann et al. .......... 378/196 |
| 6,869,217 B2 | * | 3/2005 | Rasche et al. ............... 378/197 |
| 2001/0005410 A1 | | 6/2001 | Rasche et al. |
| 2003/0048868 A1 | | 3/2003 | Bailey et al. |
| 2004/0024300 A1 | | 2/2004 | Graf |
| 2004/0122311 A1 | * | 6/2004 | Cosman ..................... 600/427 |
| 2005/0201516 A1 | | 9/2005 | Ruchala et al. |
| 2005/0228255 A1 | * | 10/2005 | Saracen et al. .............. 600/407 |
| 2006/0050847 A1 | * | 3/2006 | Jaffray et al. ................. 378/65 |
| 2006/0203958 A1 | * | 9/2006 | Nagamine et al. ............. 378/20 |

FOREIGN PATENT DOCUMENTS

| | | |
|---|---|---|
| DE | 197 46 956 A1 | 5/1999 |
| DE | 198 55 213 C2 | 3/2001 |
| DE | 199 58 864 A1 | 6/2001 |
| DE | 199 63 440 A1 | 7/2001 |
| DE | 20109313 U | 8/2001 |
| DE | 198 27 022 C2 | 1/2002 |
| DE | 101 47 160 C1 | 4/2003 |
| DE | 103 44 871 A1 | 5/2005 |
| EP | 0 220 501 A | 5/1987 |
| EP | 0 220 501 A1 | 5/1987 |
| EP | 0 220 501 B1 | 5/1989 |
| EP | 1 358 908 A1 | 11/2003 |
| JP | 08 266650 A | 10/1996 |
| JP | 08266650 | 10/1996 |
| WO | WO 03076003 A2 | 9/2003 |

OTHER PUBLICATIONS

International Search Report dated Dec. 16, 2005.
European Patent Office Action dated Nov. 5, 2007 and English translation.
European International Search Report dated Nov. 8, 2007.
Jakel, et al., "Treatment Planning for heavy ion irradiation", Physica Medica, vol. XIV, Supplement 1, Jul. 1998, pp. 53-62.
German Office Action for DE 10 2004 062 473.9-34 dated Jul. 15, 2005 and English translation.
J.E. Katuin, et al., "The Use of Industrial Robot Arms for High Precision Patient Positioning", CAARI 2002, Conference Denton, USA 2002.
T. Kamada, et al., "A Horizontal CT System Dedicated to Heavy-ion Beam Treatment", Radiotherapy and Oncology, vol. 50, 1999, pp. 235-237.
PCT form PCT/ISA/237 and PCT/ISA/210 for PCT/EP2005/054665 International Search Report and Written Opinion, including English translation.
Second Chinese Office Action dated Oct. 15, 2009 for corresponding Chinese Patent Application No. 200580022680.6 (with English translation).

* cited by examiner

MEDICAL RADIOTHERAPY ASSEMBLY

The present patent document is a national stage entry of PCT Application Serial Number PCT/EP2005/054665, filed Sep. 19, 2005, designating the United States, which is hereby incorporated by reference. This application also claims the benefit of DE 10 2004 048 216.0, filed Sep. 30, 2004, which is hereby incorporated by reference.

BACKGROUND

The present embodiments relate to a medical radiotherapy assembly.

In radiation therapy using heavy ions, tumors are bombarded with accelerated particles. A particle accelerator forms a particle beam using a beam exit that is fixed in space. During the treatment, the patient must be put into an exact, predefined position, so that the tumor is located at the isocenter of the particle beam. Depending on the position of the tumor in the body, different irradiation positions (fields) are provided for the patient. For instance, the patient is positioned in either a horizontal or a sitting position in front of the particle emitter.

It is therefore necessary in the field of radiation therapy to determine the exact position of the tumor. For this purpose, imaging diagnosis methods are employed. German Patents DE 189 55 213 C2 and DE 189 27 022 C2 or in European Patent Disclosure EP 0 220 501 B1 disclose X-ray diagnostic devices. The tumor position is typically shown on the patient directly using external markings, skin markings, or on immobilizing masks.

Depending on the type and size of tumor, in therapy planning, the number of individual radiation treatments (fractions) required to securely destroy the tumor is defined. Typically, 20-30 radiation treatments over a period of several weeks are performed per patient.

Prior to the irradiation, the patient is brought to a radiation room with a beam exit window for the particle beam. The patient is immobilized or fixed on a patient support. The term "patient support" is understood here generally to include a cot or a chair on which the patient is immobilized. In accordance with the markings located on the skin or immobilizing masks, the patient is moved into the fixed isocenter that is marked by lasers, before the radiation therapy is begun. In addition to the beam exit window, a stationary imaging device is also provided in the radiation treatment room. The stationary imaging device can verify the tumor position from anatomical landmarks. After the verification, the patient is moved from his imaging position to an irradiation position.

Changes in the position of the tumor between the time of diagnosis and the time of each radiation treatment can lead to reduced effectiveness of the radiation therapy. The orientation of the patient into the isocenter based on the markings also involves imprecision. Even if the tumor position is verified immediately before the radiation treatment, exact positioning is difficult because the patient is moved from the imaging position to the irradiation position.

SUMMARY

The present embodiments may obviate one or more of the drawbacks or limitations of related art. For example, in one embodiment, a medical radiotherapy assembly is able to provide efficient and accurate radiation therapy.

In one embodiment, a radiotherapy assembly includes an exit window for a particle beam. The exit window includes a beam exit that is fixed in space. A patient support device with a patient support that is disposed in front of the exit window can be put in an irradiation position that is suitable for irradiating a patient.

In one embodiment, the assembly has a diagnostic device or imaging device for determining or verifying the position of a tumor to be irradiated. The imaging device is an X-ray device and includes an X-ray radiation source and an X-ray detector diametrically opposite the radiation source. The imaging device can be moved in space around the patient support that is located in the irradiation position.

In one embodiment, The X-ray source and the X-ray detector are secured to a common and mechanically rigid support arm. In this embodiment, the X-ray source and X-ray detector are each positioned at the point relative to one another. For the motion in space, only the support arm has to be suitably triggered and moved. Thus, two independent motions in space are not needed, making the triggering and moving simple.

In one embodiment, the support arm is supported and triggerable in such a way that both an angular motion about the longitudinal axis defined by the particle beam and an orbital motion about an axis perpendicular to the longitudinal axis can be executed. This embodiment is capable of imaging diagnosis for any possible irradiation position of the patient. The two degrees of rotational freedom and the support arm that is open on one side are superimposed so that all the diagnostic positions for verifying the tumor can be assumed, regardless of the position of the patient at the time.

In one embodiment, the radiotherapy assembly includes a particle emitter that is combined with an imaging device in such a way that the patient, located on the patient support, can be subjected to both imaging and therapy in one and the same position. A determination or verification of the position of the tumor is made possible directly in the irradiation position. The imaging is performed directly before or even during the radiation treatment. In this embodiment, there is no shifting of the patient from the imaging to the radiation treatment. Shifting the patient always has the intrinsic risk of shifting the tumor. In this embodiment, an exact positioning of the tumor in the isocenter of the particle emitter is made possible because the position of the tumor is verified in the irradiation position. The overall radiation therapy is highly efficient. Because the imaging device is freely movable in space, it is unimportant what position the patient is in, whether seated or lying down, while the radiation therapy is performed.

In one embodiment, a method to be performed with a radiotherapy assembly includes a position verification that is performed to determine the tumor position. The position verification is possible in any arbitrary therapy position of the patient because of a special embodiment of the radiotherapy assembly. For the position verification, the tumor position is determined from two-dimensional projection images. Alternatively, the position verification for determining the tumor position is determined on the basis of three-dimensional slice images.

In one embodiment, the position verification as well as the actual radiation treatment are both made possible with the patient lying down and with the patient seated and in any suitable therapy position of the patient. In one embodiment, the patient support is or can be modified as a cot for a horizontal irradiation position or as a chair for a seated irradiation position of the patient. In this embodiment, it is possible, given a stationary beam exit, to irradiate the patient in arbitrary irradiation positions. Frontal irradiation is also made possible because of the seated position. This variability dictated by this embodiment makes considerable cost savings possible, compared to previous systems, since a gantry, with the aid of which the angle of radiation of the particle beam is set in a complicated and hence expensive way, can be dispensed with.

In one embodiment, the equipment of the particle emitter and the imaging device are combined. In the course of a radiation treatment, the position of the tumor is verified or monitored, and the patient's position is actively monitored.

In one embodiment, two-dimensional projection images, for instance, are made and the images produced are compared, with the aid of a suitable image evaluation, with previously developed three-dimensional images of the tumor. Changes in the position of the tumor can be reacted to online, or during a given radiation treatment, by shifting the patient under automatic control, to the optimal irradiation position.

The highly flexible positionability of the diagnostic device makes it possible with one and the same imaging device, that is, one and the same radiation source and radiation detector pair, to produce images of the tumor for various irradiation positions. In comparison to stationary X-ray diagnostic devices, each of which is provided for making images in only one patient position, a pronounced simplification in terms of equipment and a more-economical embodiment are achieved.

In one embodiment, the X-ray device uses a conventional X-ray device, for instance for producing two-dimensional projection images or also for producing three-dimensional low-contrast images. When producing three-dimensional low-contrast images, the patient is irradiated with a fanned-out X-ray beam, and the signals received by the radiation detector are evaluated to generate a three-dimensional image. This imaging method is also known by the term 3D cone beam reconstruction.

In one embodiment, the support arm includes C- or U-shaped mechanical load-bearing constructions that are open to one side. The support arm, in arclike fashion, spans the patient support located between the radiation detector and the radiation source.

In one embodiment, the support arm is supported and triggerable in such a way that for both the angular motion and for the orbital motion, a rotary angle of at least 180° can be executed. Comprehensive image information, for example, for a three-dimensional image production, can be obtained. If a fanned-out X-ray beam is used for a 3D cone beam process, the rotary motion for the angular motion and orbital motion amounts to at least 180°, plus the fan width of the X-ray beam.

In one embodiment, the support arm is rotatably supported on the particle emitter. The particle emitter and the diagnostic device form a combined unitary structural unit. Because of the structural combination, the relative position between the radiation source and the radiation detector with respect to the isocenter of the particle emitter is exactly defined.

In one embodiment, the support arm is a multiaxial robot arm, for example, one arm with six axes. Free motion in space is made possible without or virtually without limitations, so that individual requirements can easily be taken into account because of the guidance via a multiaxial robot arm. In both variants, a load-bearing structure of the diagnostic device is located in stationary form in space, and only the support arm is freely movable in space.

In one embodiment, the patient support is movable in controlled fashion to a predefined irradiation position. The patient can be moved to a desired position after the verification of the tumor position.

A common control unit is provided. The common control unit controls two devices, namely the diagnostic device and the patient support device, in a way adapted to one another. The patient support with the patient immobilized on it is moved into the required irradiation position based on the isocenter of the particle beam and the tumor position, has been ascertained with the aid of the diagnostic device. In one embodiment, determining the position of the tumor from the X-ray images is done either automatically by suitable automatic image recognition processes or manually by skilled medical personnel who inform the control unit of the position of the tumor via a suitable input device.

In one embodiment, a plurality of exit windows for the particle beam are provided at predetermined angles relative to the patient's position. Because the diagnostic device is movable in space around the patient support located in the irradiation position, the same diagnostic device is also suitable for radiation therapy applications involving a plurality of exit windows for the particle beam. In one embodiment, the diagnostic device is used in combination with a plurality of exit windows, disposed at defined angles, for particle beams, each with exit windows that are fixed in space.

DETAILED DESCRIPTION

Figure 1:
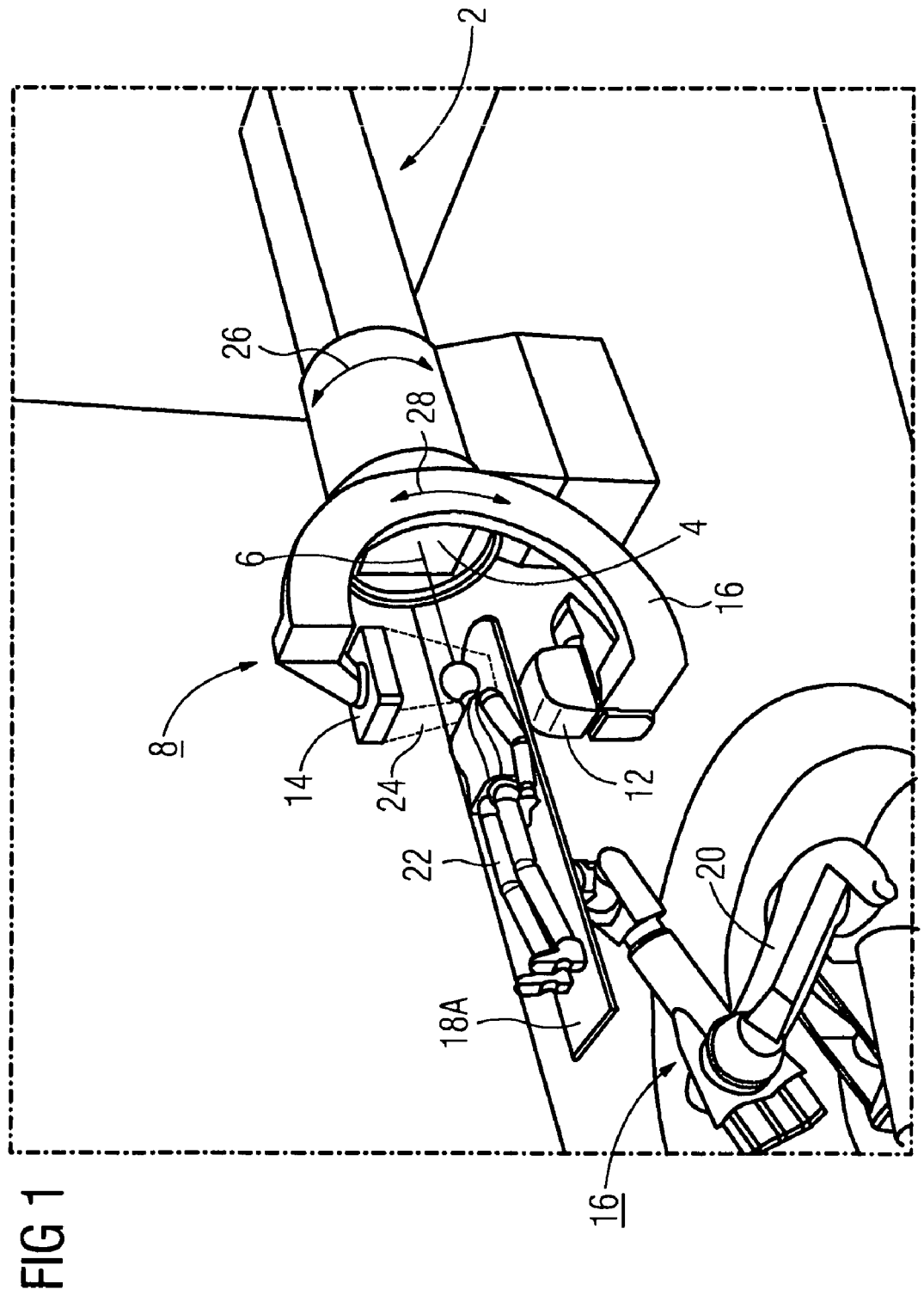
FIG. 1 shows one embodiment of a radiotherapy assembly that includes a rotatably supported X-ray diagnostic device and a C-arch support arm in one irradiation position.

Generally, in the drawings, elements that function the same are identified by the same reference numerals.

The medical radiotherapy assembly includes a particle accelerator for generating a particle beam comprising heavy ions, hereinafter called a particle emitter. The particle emitter includes a barrel 2 and an exit window 4 on the front. When the exit window 4 is at a predefined position, a particle beam 6 emerges during operation. The barrel 2 and the exit window 4 are disposed in stationary fashion in space. In an alternate embodiment (not shown), a plurality of fixed exit windows 4 are disposed in space at defined angles.

An X-ray diagnostic device 8 includes a support arm 10A, 10B, which has an X-ray source 12 and an X-ray detector 14 each disposed at diametrically opposed positions.

A patient support device 16 includes a patient support 18, which is movable in controlled fashion via a first multiaxial robotical support arm 20. The term "patient support" 18A, 18B is a device on which a patient 22 is put into a position intended for the radiation therapy. This position can be either a seated or a horizontal position. The patient support 18A, 18B may be a cot for a horizontal position of the patient 22 or a chairlike structure for a seated position of the patient 22.

In one embodiment, the X-ray diagnostic device 8 and the exit window 4 are combined, such that an X-ray image for determining or verifying the position of a tumor can be made in the treatment position of the patient 22 intended for the radiation therapy. The X-ray diagnostic device 8 is suitable for both two-dimensional projection images and for three-dimensional low-contrast images and is able to generate 3D cone beam images.

In exemplary embodiments, as shown in the Figures, a fan-shaped X-ray beam 24 produces the 3D cone beam images, or generates three-dimensional images of the tumor to be irradiated. A known method for image generation and image evaluation may be used. To produce 3D X-ray images, the fan-shaped beam 24 is movable by at least 180°, plus the fan angle, around the patient 22. Regardless of the particular irradiation position of the patient 22, verification of the tumor can be done with one and the same diagnostic device. The position verification is independent of whether the patient 22 is lying down or in a seated position, that is, whether he is oriented longitudinally to the particle beam 6 or transversely to it. A definitive factor for this variability is the disposition of the X-ray diagnostic device 8 in such a way that it is freely movable in space.

The support arm 10A, 10B is open to one side. In this embodiment, the support arm 10A, 10B may include a U-shape or C-shape. The support arm 10A, 10B can be moved without problems above the patient and the patient is positioned between the radiation source 12 and the radiation detector 14. For the rotatability by more than 180° around the patient 22, the support arm 10A, 10B can execute an angular motion around the longitudinal axis defined by the particle beam 6. As shown in the Figures, the angular motion is indicated by a double arrow 26. Alternatively, the support arm 10A, 10B is also capable of executing an orbital motion about an axis perpendicular to the particle beam 6. This orbital motion is represented by a further double arrow 28.

Once the patient 22 has assumed a defined treatment position, the diagnostic device 8 executes a 180° rotation (plus the fan angle of the X-ray beam) in only one of the two directions of motion. The diagnostic device 8 executes either an angular motion 28 about the longitudinal axis or an orbital motion 28 about a further pivot axis that is perpendicular to the longitudinal axis. The location of this further pivot axis in space is variable and depends on the angular rotary position at the time of the support arm 10A, 10B.

Figure 2:
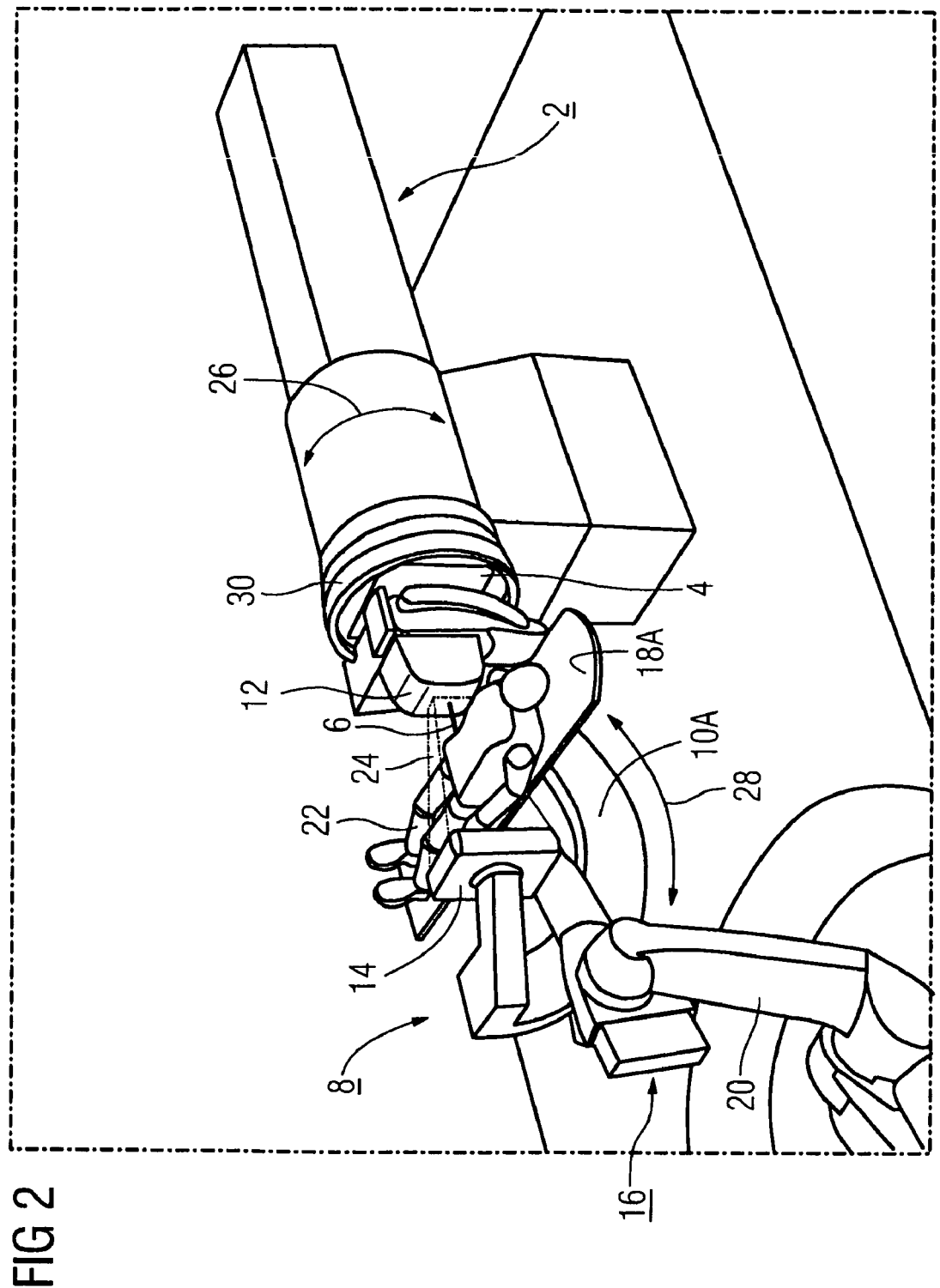
FIG. 2 shows one embodiment of a radiotherapy assembly that includes a rotatably supported X-ray diagnostic device and a C-arch support arm in one irradiation position.
Figure 3:
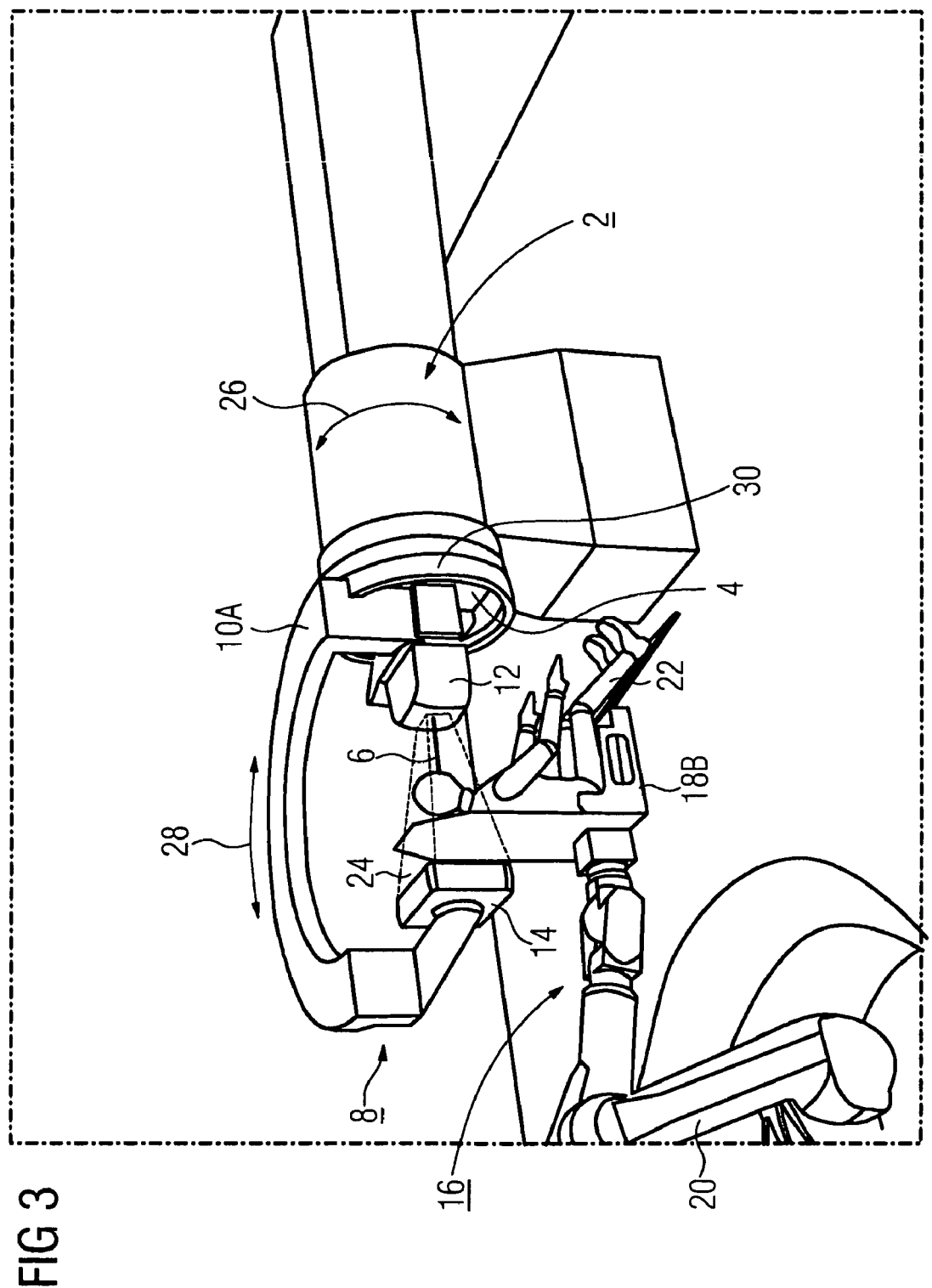
FIG. 3 shows one embodiment of a radiotherapy assembly that includes a rotatably supported X-ray diagnostic device and a C-arch support arm in one irradiation position.

In the exemplary embodiments of FIGS. 1 through 3, the support arm 10A is embodied as a C-arch, which has the radiation source 12 and the detector 14, respectively, on the ends of its arch. The support arm 10A, for executing the angular motion 26, is supported via a rotary ring 30 that extends annularly around the barrel 2. The support arm 10A can be rotated about the longitudinal axis defined by the particle beam 6 via the rotary ring 30. For executing the orbital motion 28, the support arm 10A is supported displaceably on the rotary ring 30 itself. For example, the support arm 10A is guided by a guide rail or by a mesh toothing between the rotary ring 30 and the support arm 10A. An orbital rotation of 180° can be executed in any angular rotary position. Conversely, an angular rotary motion 26 about at least 180° can be executed in any orbital rotary position. According to these embodiments, rotary motions of about 360° are possible in each case. The rotary motions are limited essentially by the position of the patient support 18A, 18B.

In the exemplary embodiment of FIG. 1, the patient 22 is in a horizontal irradiation position, oriented longitudinally to the particle beam 6, for treatment of a brain tumor. In this embodiment, for 3D image verification of the position of the brain tumor, the support arm 10A is rotated around the head of the patient 22 by rotation of the rotary ring 30 by at least 180° in the angular direction 26.

In the exemplary embodiment shown in FIG. 2, the patient 22 is located transversely to the particle beam 6, in a horizontal position. The support arm 10A is in a fixed angular position. For X-ray imaging, the support arm 10A is pivoted by at least 180° in the orbital direction 28 around the torso of the patient 22. A rotary motion in the angular direction 26 does not take place in this embodiment.

In the exemplary embodiment shown in FIG. 3, the patient 22 is in a seated treatment position. For taking the X-ray image, once again a motion of the support arm 10A takes place in the orbital direction 28.

Figure 4:
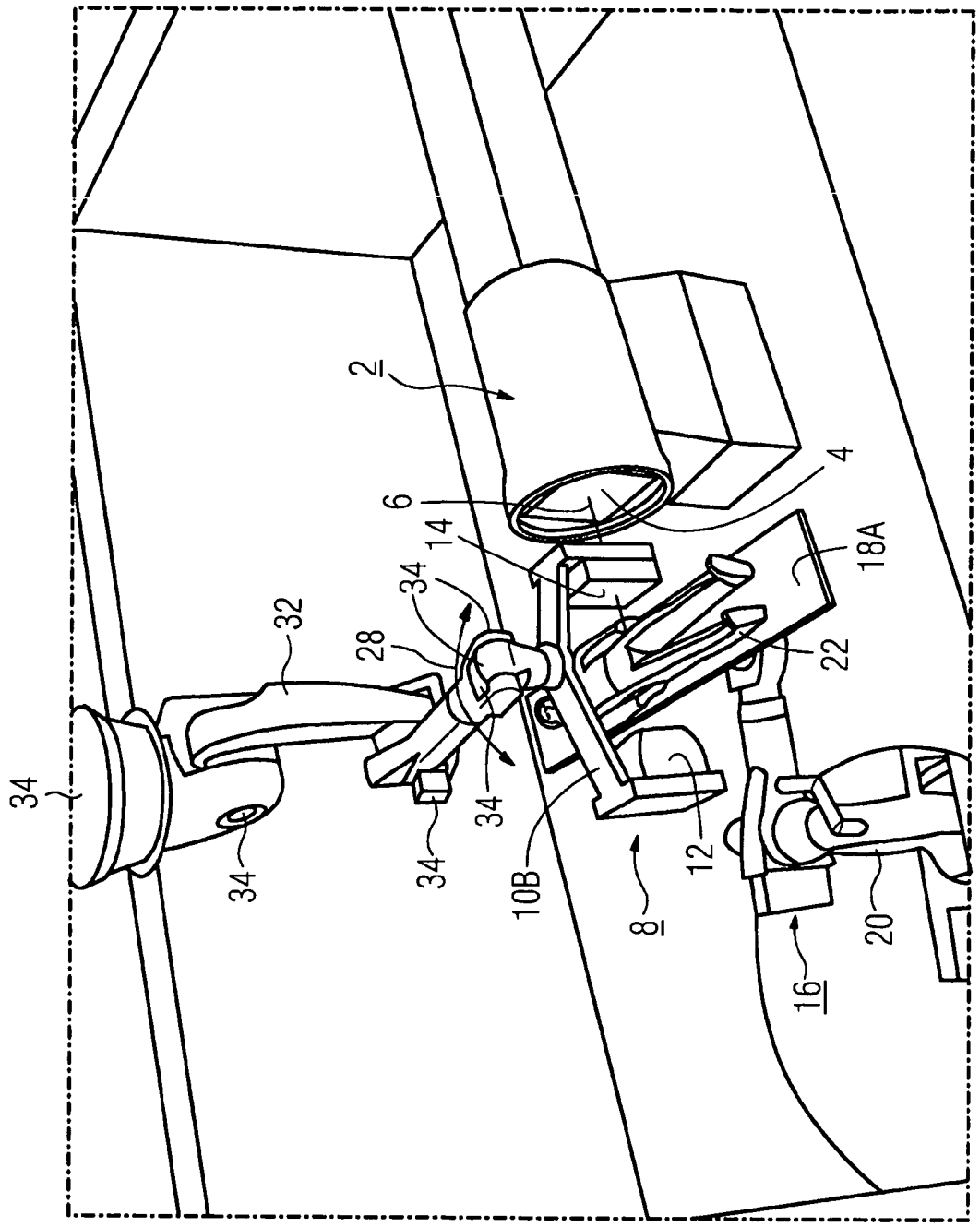
FIG. 4 shows another embodiment of the radiotherapy assembly that includes a support arm secured to a multiaxial robot arm.
Figure 5:
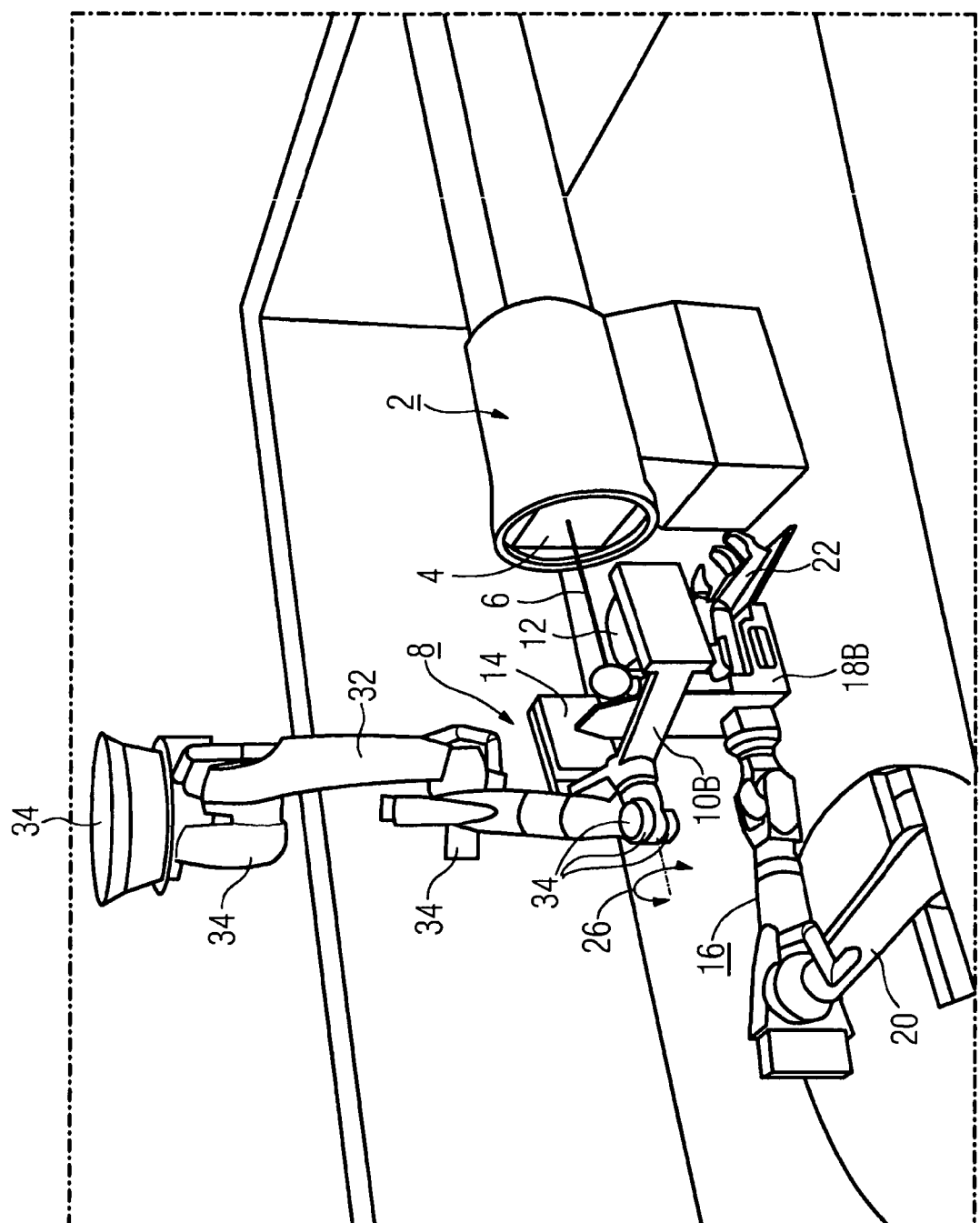
FIG. 5 shows one embodiment of the radiotherapy assembly that includes a support arm secured to a multiaxial robot arm.

As shown in FIGS. 4 and 5, the support arm 10B is secured to a second support arm 32, which has six axes. The second robot arm 32 is secured to the ceiling of a room in this exemplary embodiment. Because of the multiaxial embodiment of the second robot arm 32, the support arm 10B can be positioned at arbitrary points in the room that are accessible by the second robot arm 32. For performing the angular rotary motion 26 and the orbital rotary motion 28, the second robot arm 32 has a plurality of pivot joints 34. For recording the X-ray image, an at least 180° rotation is performed, either in the orbital direction 28 or in the angular direction 26, depending on the particular irradiation position in which the patient 22 is located at the time.

The X-ray diagnostic device 8, the patient support device 16, and optionally the particle accelerator are preferably driven by a common control unit that is adapted to each device. In one embodiment, the patient 22 is put into a preliminary treatment position for the radiation therapy. In this embodiment, the patient 22 is immobilized on the patient support 18A, 18B, and the patient support 18A, 18B and is then moved by the first robot arm 20 into the desired preliminary treatment position. In this position, the position of the tumor is determined and verified with the aid of the X-ray device 8. The immobilized patient 22 is moved, automatically and under control, into the optimal irradiation position via the patient support device 8, so that the tumor is positioned in the isocenter. The correct positioning is verified with the X-ray device 8.

The determination of the tumor position is done either automatically or by evaluation by professional medical persons of the images made. After the patient 22 is positioned, the particle beam 6 is generated, and the patient 22 is irradiated. In each of the drawings, the particle beam 6 is shown in dashed lines, in order to indicate that the radiation treatment with the particle beam 6 is completed after the X-ray images have been made.

With the aid of a control unit and monitoring unit, not shown in further detail here, the patient 22 is preferably automatically moved into the correct treatment position for the radiation treatment.

Various embodiments described herein can be used alone or in combination with one another. The forgoing detailed description has described only a few of the many possible implementations of the present invention. For this reason, this detailed description is intended by way of illustration, and not by way of limitation. It is only the following claims, including all equivalents that are intended to define the scope of this invention.

The invention claimed is:

1. A medical ion radiotherapy assembly comprising:
an exit window for a particle beam,
a patient support device that includes a patient support that is disposable in front of the exit window into an irradiation position suitable for irradiating a patient, and
a diagnostic device that is operable to determine the position of a tumor to be irradiated, the diagnostic device including a radiation source and a diametrically opposed radiation detector which are secured to a common support arm;

the support arm being operably supported in such a way that both an angular motion about a longitudinal axis defined by the particle beam and an orbital motion about an axis perpendicular to the longitudinal axis can be executed, the radiation source and the radiation detector being movable in space around the patient support that is in the irradiation position; and a control unit that controls the patient support device and the diagnostic device, the control unit being operable to control a position of the patient support device based on an output of the diagnostic device and control the diagnostic device into a position for verifying that the tumor is located in an isocenter of the particle beam based on the position of the patient support device.

2. The ion radiotherapy assembly as defined by claim 1, wherein the diagnostic device is operable to determine the tumor position from two-dimensional projection images in any arbitrary irradiation position of the patient.

3. The ion radiotherapy assembly as defined by claim 2, wherein the radiation source and the radiation detector are freely movable in space around a patient support that comprises a cot for a horizontal irradiation position or a chair for a seated irradiation position.

4. The ion radiotherapy assembly as defined by claim 3, wherein the support arm is C-shaped or U-shaped.

5. The ion radiotherapy assembly as defined by claim 4, wherein a rotary motion of the support arm of about at least 180° can be executed for both the angular motion and the orbital motion.

6. The ion radiotherapy assembly as defined by claim 1, wherein the radiation source and the radiation detector are freely movable in space around a patient support that comprises a cot for a horizontal irradiation position or a chair for a seated irradiation position.

7. The ion radiotherapy assembly as defined by claim 6, wherein the support arm is C-shaped or U-shaped.

8. The ion radiotherapy assembly as defined by claim 1, wherein the support arm is C-shaped or U-shaped.

9. The ion radiotherapy assembly as defined by claim 1, wherein a rotary motion of the support arm of about at least 180° can be executed for both the angular motion and the orbital motion.

10. The ion radiotherapy assembly as defined by claim 9, wherein the support arm is retained by a multiaxial robot arm.

11. The ion radiotherapy assembly as defined by claim 1, wherein the support arm is rotatably supported on a device for generating the particle beam.

12. The ion radiotherapy assembly as defined by claim 1, wherein the patient support is movably controlled into a predefined irradiation position.

13. The radiotherapy assembly as defined by claim 1, wherein the exit window is disposed in stationary fashion in a room and is part of a device for generating an ion particle beam.

14. The ion radiotherapy assembly as defined by claim 1, wherein the diagnostic device is operable to determine the tumor position from three-dimensional slice images in any arbitrary irradiation position of the patient.

15. The ion radiotherapy assembly as defined by claim 1, wherein the support arm is rotatably supported on a device that generates the particle beam.

16. The ion radiotherapy assembly as defined by claim 15, wherein the support arm is retained by a multiaxial robot arm.

17. The ion radiotherapy assembly as defined by claim 1, comprising:
a barrel, closed by the exit window, that is operable to guide the particle beam,
wherein the support arm, that executes the angular motion at the barrel, is supported rotatably about the barrel.

* * * * *